United States Patent
Klima et al.

(10) Patent No.: US 10,213,300 B2
(45) Date of Patent: Feb. 26, 2019

(54) HYPOTUBE SHAFT WITH ARTICULATION MECHANISM

(71) Applicant: St. Jude Medical, Cardiology Division, Inc., St. Paul, MN (US)

(72) Inventors: Daniel J. Klima, Andover, MN (US); Jeffrey P. Laplante, Minneapolis, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 15/004,373

(22) Filed: Jan. 22, 2016

(65) Prior Publication Data

US 2016/0135952 A1    May 19, 2016

Related U.S. Application Data

(62) Division of application No. 13/796,398, filed on Mar. 12, 2013, now Pat. No. 9,277,990.

(Continued)

(51) Int. Cl.
| | |
|---|---|
| *A61F 2/24* | (2006.01) |
| *A61M 25/01* | (2006.01) |
| *A61B 17/00* | (2006.01) |

(52) U.S. Cl.
CPC ...... *A61F 2/2436* (2013.01); *A61B 17/00234* (2013.01); *A61F 2/2427* (2013.01);
(Continued)

(58) Field of Classification Search
CPC .. A61F 2/2427; A61F 2/82; A61F 2/95; A61F 2/962; A61F 2/2436;
(Continued)

(56) References Cited

U.S. PATENT DOCUMENTS

| | | | |
|---|---|---|---|
| 3,384,088 A | 5/1968 | Miseo | |
| 3,657,744 A | 4/1972 | Ersek | |

(Continued)

FOREIGN PATENT DOCUMENTS

| | | |
|---|---|---|
| EP | 1129744 A1 | 9/2001 |
| EP | 1157673 A2 | 11/2001 |

(Continued)

OTHER PUBLICATIONS

International Search Report and Written Opinion for Application No. PCT/US2013/039405 dated Sep. 23, 2013.

(Continued)

*Primary Examiner* — Diane Yabut
*Assistant Examiner* — Erich Herbermann
(74) *Attorney, Agent, or Firm* — Lerner, David, Littenberg, Krumholz & Mentlik, LLP

(57) ABSTRACT

A delivery device for a prosthetic heart valve includes a shaft, a sheath, and a pull wire. The shaft has a proximal end, a distal end, and a longitudinal axis. The sheath is attached to the shaft and is rotatable about an axis transverse to the longitudinal axis of the shaft. The pull wire is mechanically coupled to the sheath such that movement of the pull wire rotates the sheath relative to the shaft. The sheath may be in a first position relative to the shaft when a distal end of the pull wire is in a first position and may be in a second position when the distal end of the pull wire is in a second position. Deflection of the sheath relative to the shaft enables a prosthetic valve to be axially aligned with the native valve annulus for deployment.

25 Claims, 12 Drawing Sheets

Related U.S. Application Data

(60) Provisional application No. 61/643,149, filed on May 4, 2012.

(52) U.S. Cl.
CPC ............... *A61M 25/0147* (2013.01); *A61B 2017/00243* (2013.01); *A61B 2017/00318* (2013.01); *A61F 2250/0006* (2013.01); *A61M 2025/015* (2013.01)

(58) Field of Classification Search
CPC .......... A61M 25/0133; A61M 25/0067; A61M 25/0068; A61M 25/0069; A61M 25/0074; A61M 25/008; A61M 25/0082; A61M 25/0147; A61M 201/015; A61B 1/00137
USPC ................. 623/2.11, 1.26; 600/141–142; 606/141–142
See application file for complete search history.

(56) References Cited

U.S. PATENT DOCUMENTS

| | | | |
|---|---|---|---|
| 3,724,238 A | 4/1973 | Retali et al. | |
| 4,423,730 A | 1/1984 | Gabbay | |
| 4,641,657 A | 2/1987 | Ellis | |
| 4,686,963 A * | 8/1987 | Cohen | A61B 1/0055 138/120 |
| 5,368,592 A | 11/1994 | Stern et al. | |
| 5,372,587 A | 12/1994 | Hammerslag et al. | |
| 5,405,344 A | 4/1995 | Williamson et al. | |
| 5,507,725 A | 4/1996 | Savage et al. | |
| 5,549,594 A | 8/1996 | Brunken | |
| 5,569,270 A | 10/1996 | Weng | |
| 5,575,799 A | 11/1996 | Bolanos et al. | |
| 5,749,881 A | 5/1998 | Sackier et al. | |
| 5,843,167 A | 12/1998 | Dwyer et al. | |
| 5,868,685 A | 2/1999 | Powell et al. | |
| 5,924,424 A | 7/1999 | Stevens et al. | |
| 5,968,068 A | 10/1999 | Dehdashtian et al. | |
| 6,077,297 A | 6/2000 | Robinson et al. | |
| 6,183,432 B1 | 2/2001 | Milo | |
| 6,306,141 B1 | 10/2001 | Jervis | |
| 6,464,684 B1 * | 10/2002 | Galdonik | A61M 25/005 604/527 |
| 6,623,518 B2 | 9/2003 | Thompson et al. | |
| 6,743,239 B1 | 6/2004 | Kuehn et al. | |
| 6,814,746 B2 | 11/2004 | Thompson et al. | |
| 6,830,584 B1 | 12/2004 | Seguin | |
| 7,018,406 B2 | 3/2006 | Seguin et al. | |
| 7,300,431 B2 | 11/2007 | Dubrovsky | |
| 7,311,730 B2 | 12/2007 | Gabbay | |
| 7,510,572 B2 | 3/2009 | Gabbay | |
| 7,637,905 B2 | 12/2009 | Saadat et al. | |
| 7,682,390 B2 | 3/2010 | Seguin | |
| 7,803,185 B2 | 9/2010 | Gabbay | |
| 7,811,277 B2 | 10/2010 | Boulais | |
| 9,227,990 B2 | 1/2016 | Phull et al. | |
| 2003/0050694 A1 | 3/2003 | Yang et al. | |
| 2003/0233108 A1 | 12/2003 | Gellman et al. | |
| 2004/0210304 A1 | 10/2004 | Seguin et al. | |
| 2005/0137622 A1 | 6/2005 | Griffin | |
| 2005/0137695 A1 | 6/2005 | Salahieh et al. | |
| 2005/0137697 A1 | 6/2005 | Salahieh et al. | |
| 2005/0165352 A1 | 7/2005 | Henry et al. | |
| 2005/0177138 A1 | 8/2005 | Dubrovsky | |
| 2005/0222604 A1 | 10/2005 | Schaeffer | |
| 2006/0058872 A1 | 3/2006 | Salahieh et al. | |
| 2006/0074484 A1 | 4/2006 | Huber | |
| 2006/0089704 A1 * | 4/2006 | Douglas | A61F 2/07 623/1.12 |
| 2006/0100687 A1 | 5/2006 | Fahey et al. | |
| 2006/0106415 A1 | 5/2006 | Gabbay | |
| 2006/0142848 A1 | 6/2006 | Gabbay | |
| 2006/0167468 A1 | 7/2006 | Gabbay | |
| 2006/0235502 A1 | 10/2006 | Belluche et al. | |
| 2006/0259120 A1 | 11/2006 | Vongphakdy et al. | |
| 2007/0010876 A1 | 1/2007 | Salahieh et al. | |
| 2007/0027534 A1 | 2/2007 | Bergheim et al. | |
| 2007/0043259 A1 | 2/2007 | Jaffe et al. | |
| 2007/0043435 A1 | 2/2007 | Seguin et al. | |
| 2007/0055358 A1 | 3/2007 | Krolik et al. | |
| 2007/0073376 A1 | 3/2007 | Krolik et al. | |
| 2007/0073391 A1 | 3/2007 | Bourang et al. | |
| 2007/0088431 A1 | 4/2007 | Bourang et al. | |
| 2007/0112422 A1 | 5/2007 | Dehdashtian | |
| 2007/0162100 A1 | 7/2007 | Gabbay | |
| 2007/0168013 A1 | 7/2007 | Douglas | |
| 2007/0203575 A1 | 8/2007 | Forster et al. | |
| 2007/0219411 A1 * | 9/2007 | Dejima | A61B 17/3478 600/141 |
| 2007/0239271 A1 | 10/2007 | Nguyen | |
| 2007/0244552 A1 | 10/2007 | Salahieh et al. | |
| 2007/0250113 A1 | 10/2007 | Hegeman et al. | |
| 2008/0065122 A1 | 3/2008 | Stack et al. | |
| 2008/0071369 A1 | 3/2008 | Tuval et al. | |
| 2008/0097398 A1 * | 4/2008 | Mitelberg | A61M 25/0043 604/525 |
| 2008/0147160 A1 | 6/2008 | Ghione et al. | |
| 2008/0147182 A1 | 6/2008 | Righini et al. | |
| 2008/0228223 A1 | 9/2008 | Alkhatib | |
| 2009/0054975 A1 | 2/2009 | del Nido et al. | |
| 2009/0062606 A1 | 3/2009 | Ueda et al. | |
| 2009/0062839 A1 | 3/2009 | Kurrus | |
| 2010/0004740 A1 | 1/2010 | Seguin et al. | |
| 2010/0204708 A1 | 8/2010 | Sharma | |
| 2010/0228152 A1 * | 9/2010 | Fisher | A61B 17/320758 600/585 |
| 2010/0228191 A1 * | 9/2010 | Alvarez | A61B 1/0055 604/95.01 |
| 2010/0286768 A1 * | 11/2010 | Alkhatib | A61F 2/2418 623/2.11 |
| 2010/0298931 A1 | 11/2010 | Quadri et al. | |
| 2011/0098800 A1 | 4/2011 | Braido et al. | |
| 2011/0207999 A1 | 8/2011 | Torisawa et al. | |
| 2011/0224678 A1 | 9/2011 | Gabbay | |
| 2011/0245917 A1 * | 10/2011 | Savage | A61F 2/2427 623/2.11 |
| 2011/0295242 A1 * | 12/2011 | Spivey | A61B 17/07207 606/1 |
| 2012/0078350 A1 | 3/2012 | Wang et al. | |
| 2012/0259314 A1 * | 10/2012 | Guo | A61B 17/22 604/509 |
| 2012/0303111 A1 | 11/2012 | Dwork et al. | |
| 2013/0060328 A1 | 3/2013 | Rothstein | |
| 2013/0103047 A1 | 4/2013 | Steingisser et al. | |
| 2013/0274870 A1 | 10/2013 | Lombardi et al. | |
| 2013/0297012 A1 | 11/2013 | Willard | |
| 2013/0297102 A1 | 11/2013 | Hughes et al. | |

FOREIGN PATENT DOCUMENTS

| | | |
|---|---|---|
| EP | 1716822 A1 | 11/2006 |
| EP | 1926455 A2 | 6/2008 |
| FR | 2765098 A1 | 12/1998 |
| WO | 9510317 A1 | 4/1995 |
| WO | 2006138173 A2 | 12/2006 |
| WO | 07071436 A2 | 6/2007 |
| WO | 08070797 A2 | 6/2008 |
| WO | 10051025 A1 | 5/2010 |
| WO | 10087975 A1 | 8/2010 |
| WO | 2010127162 A1 | 11/2010 |
| WO | 2012112469 A2 | 8/2012 |
| WO | 2013166355 A1 | 11/2013 |
| WO | 2014130160 A1 | 8/2014 |

OTHER PUBLICATIONS

Quaden, Rene, et al., Percutaneous aortic valve replacement: resection before implantation, 836-840, European J. of Cardio-thoracic Surgery, 27 (2005).

(56) References Cited

OTHER PUBLICATIONS

Ruiz, Carlos, Overview of PRE-CE Mark Transcatheter Aortic Valve Technologies, Euro PCR, May 25, 2010.
International Search Report and Written Opinion for Application No. PCT/US2014/054025 dated Nov. 19, 2014.
International Search Report and Written Opinion for Application No. PCT/US2014/055053 dated Nov. 24, 2014.
International Search Report for Application No. PCT/US2013/078306 dated May 2, 2014.

* cited by examiner

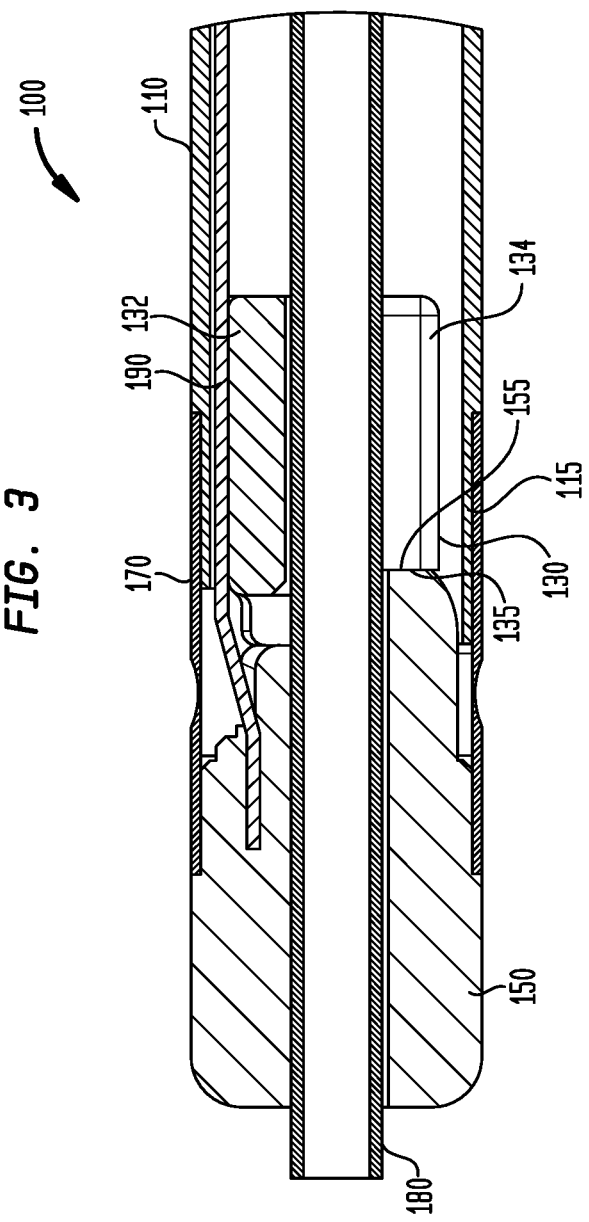

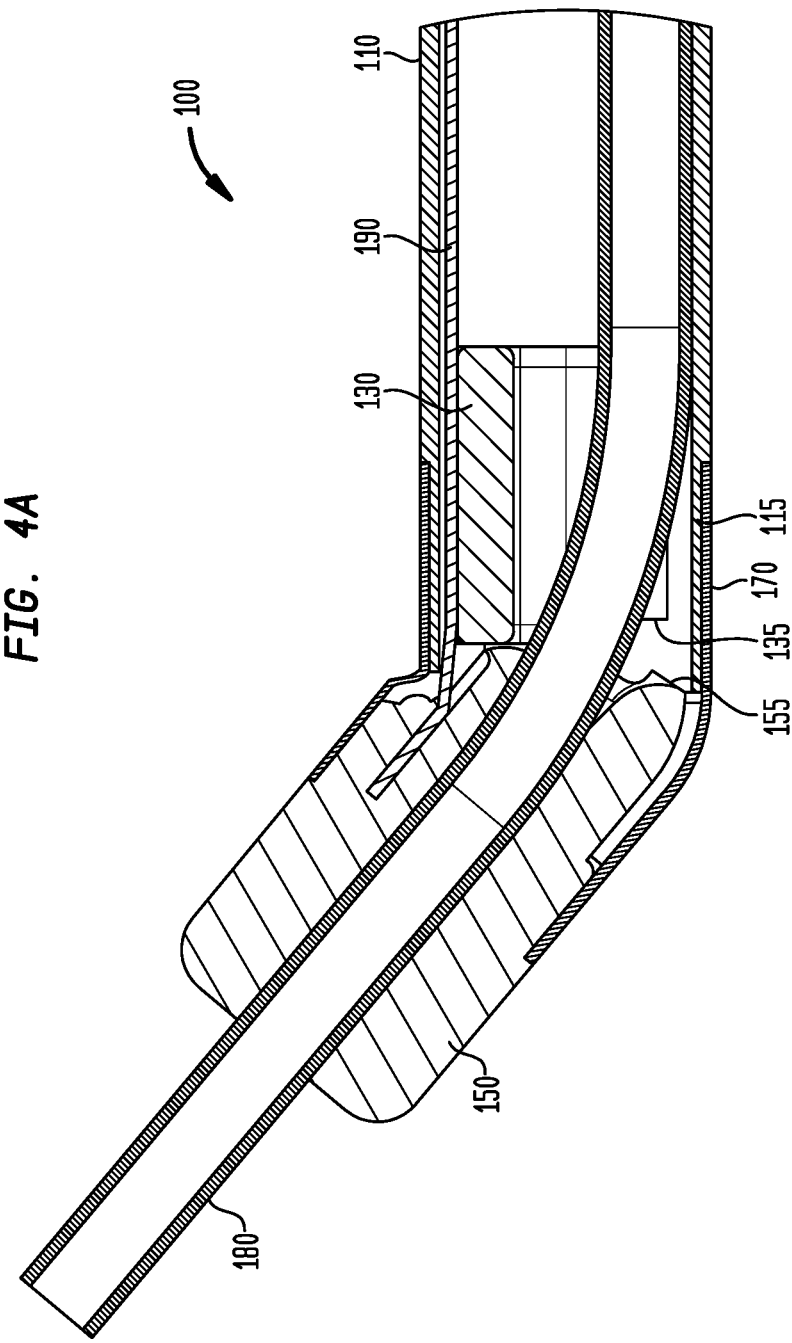

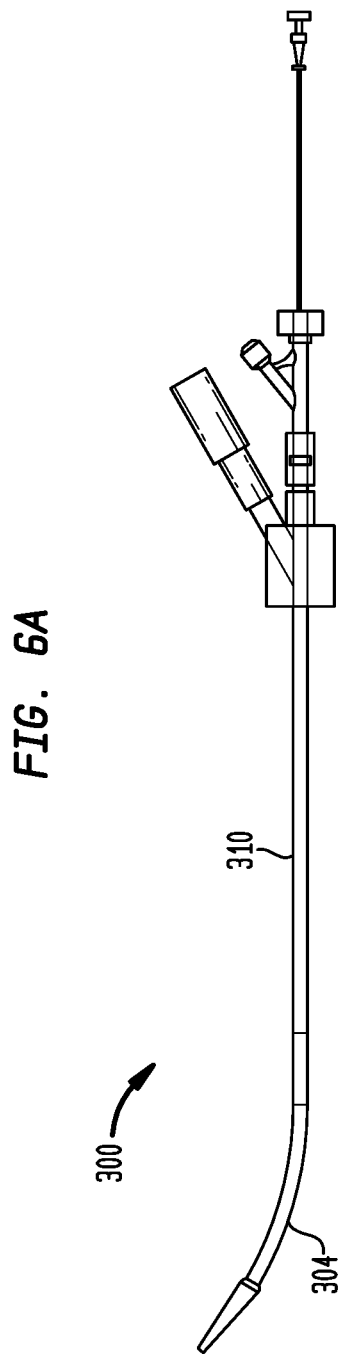

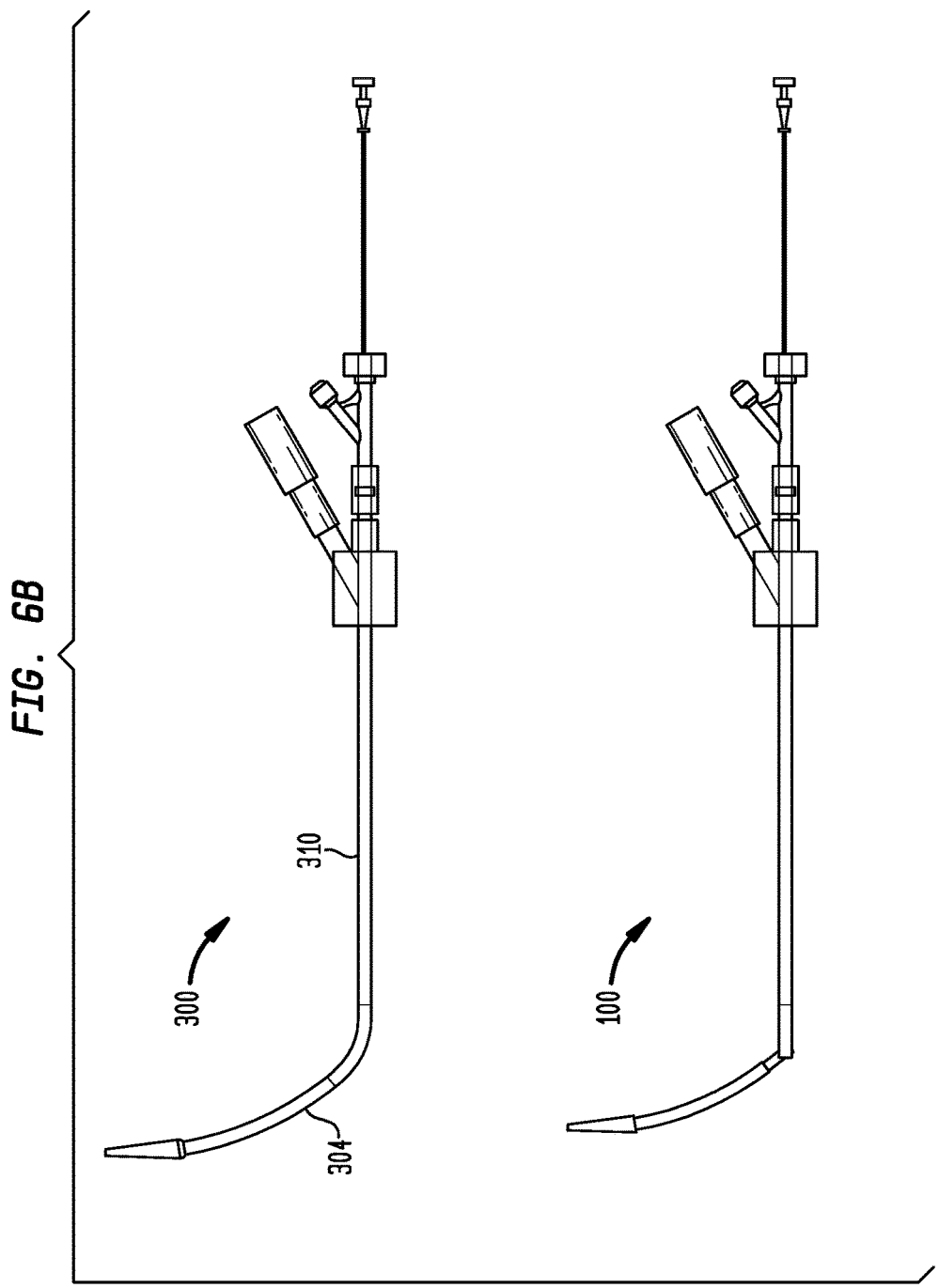

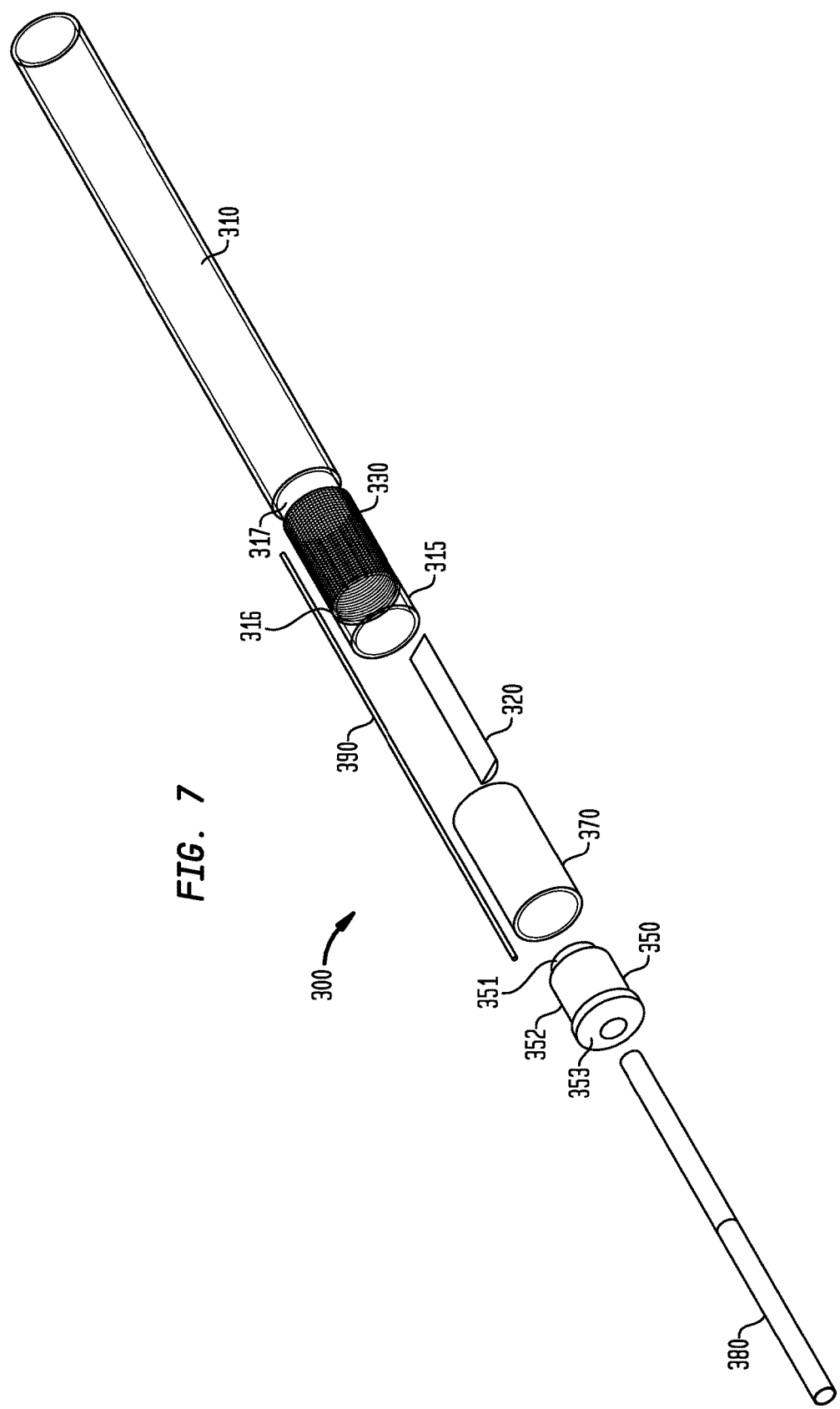

HYPOTUBE SHAFT WITH ARTICULATION MECHANISM

CROSS REFERENCE TO RELATED APPLICATION

The present application is a divisional of U.S. patent application Ser. No. 13/796,398 filed Mar. 12, 2013, and claims the benefit of the filing date of U.S. Provisional Patent Application No. 61/643,149 filed May 4, 2012, the disclosures of which are hereby incorporated herein by reference.

BACKGROUND OF THE INVENTION

The present invention is related to heart valve replacement, and more particularly to devices, systems, and methods for transcatheter delivery of collapsible prosthetic heart valves.

Prosthetic heart valves that are collapsible to a relatively small circumferential size may be delivered into a patient less invasively than valves that are not collapsible. For example, a collapsible valve may be delivered into a patient via a tube-like delivery apparatus such as a catheter, a trocar, a laparoscopic instrument, or the like. This collapsibility may avoid the need for a more invasive procedure such as full open-chest, open-heart surgery.

Collapsible prosthetic heart valves typically take the form of a valve structure mounted on a stent. To place such a valve into a delivery apparatus and ultimately into a patient, the valve must first be collapsed or crimped to reduce its circumferential size. For example, a conventional collapsible prosthetic valve is typically collapsed and retained in a collapsed state by a sheath for delivery into the patient, for example, through a femoral artery or through the apex of the heart.

An end of a guide wire may be inserted percutaneously into the artery or the heart of a patient just beyond a desired implant site to establish a guide for an implantable delivery device to follow. The desired implant site is often at or near the annulus of the patient's heart valve that is to be replaced by the prosthetic valve. Once the delivery apparatus containing the prosthetic valve has reached this site, the valve may be deployed or released from the delivery apparatus and re-expanded to full operating size. For self-expanding valves, the stent automatically begins to expand as the sheath covering the valve is withdrawn.

In certain transapical delivery systems employing self-expanding aortic valves, for example, after the delivery system has been positioned for deployment, the annulus end of the valve may be unsheathed and expanded first, while the aortic end of the valve remains sheathed. Once the annulus end of the valve has expanded, it may be determined that the valve needs to be repositioned in the patient's aortic annulus. To accomplish this, the user (such as a surgeon or an interventional cardiologist) may resheath the annulus end of the valve so that the valve can be repositioned while in a collapsed state. After the valve has been repositioned, the user can again deploy the valve.

Despite the various improvements that have been made to the collapsible prosthetic heart valve delivery process, conventional delivery devices, systems, and methods suffer from some shortcomings. For example, in a conventional delivery device for collapsible prosthetic valves, such as a transapical delivery device 7 shown in FIG. 1, because the aortic valve is not directly aligned with the apex of the heart, it may be difficult to align the longitudinal axis of the distal sheath 8 normally to the geometric center of the native valve annulus 6 (i.e., axial alignment). Without axial alignment, the user will be unable to properly position the prosthetic valve relative to the native annulus 6, such that the valve will not be properly seated in the annulus and therefore will not function properly. Moreover, without axial alignment, the inner wall 3 of the aortic arch 2 may interfere with the advancement of delivery device 7 beyond the native valve annulus 6, and contact between the distal tip 9 of the delivery device and the inner wall of the aortic arch may damage the aorta.

There is therefore a need for further improvements to the devices, systems, and methods for transcatheter delivery of collapsible prosthetic heart valves. Among other advantages, the present invention may address one or more of these needs.

BRIEF SUMMARY OF THE INVENTION

In accordance with one embodiment, a device for delivering a medical aid into a patient may include an anchor having proximal and distal ends. The device may further include an arm connected to the distal end of the anchor and having a first lumen in which the arm is rotatable about the anchor at an axis substantially perpendicular to the first lumen. The device may further include a pull wire having a proximal end and a distal end that is mechanically coupled to the arm. The device may further include a flexible tube that is capable of passing through the first lumen and that has a second lumen. The arm may be in a first position when the distal end of the pull wire is in a first position and may be in a second position when the distal end of the pull wire is in a second position.

In an alternative arrangement, the flexible tube may be in a first position when the distal end of the pull wire is in a first position and the flexible tube may be in a second position when the distal end of the pull wire is in a second position. In another alternative arrangement, the arm may contact the anchor when it is in a second position such that the arm can only move in one direction. In yet another alternative arrangement, the arm may include first and second portions mechanically joined. In yet another alternative arrangement, the axis of rotation of the arm is perpendicular to an axis parallel to a central axis through the first lumen and is offset from the central axis of the first lumen. In yet another alternative arrangement, the device may further include a hollow shaft having proximal and distal ends in which the anchor may be sized to fit within the distal end of the hollow shaft. In such an arrangement, an elastomeric sleeve may cover a portion of the arm and a portion of the hollow shaft.

In accordance with another embodiment, a device for delivering a medical aid into a patient may include a hollow shaft having proximal and distal ends, a longitudinal axis, and a flexible portion between the proximal and distal ends that may be capable of bending away from the longitudinal axis. The device may further include a guide bushing having a proximal and distal ends and a first lumen in which a distal end of the bushing may be sized to matingly engage the distal end of the hollow shaft. The device may further include a pull wire having proximal and distal ends in which the distal end of the pull wire may be mechanically coupled to the guide bushing. The device may further include a flexible tube capable of passing through the first lumen of the guide bushing in which the flexible tube may have a second lumen. In such an embodiment, the guide bushing may be in a first position when the distal end of the pull wire is in a first position and the guide bushing may be in a second position when the distal end of the pull wire is in a second position.

In an alternative arrangement, the flexible tube may be in a first position when the distal end of the pull wire is in a first position and the flexible tube may be in a second position when the distal end of the pull wire is in a second position. In another alternative arrangement, the hollow shaft may have an interior surface along its entire length. In such an arrangement, the device may further include a resilient member attached to the interior surface of the hollow shaft on proximal and distal sides of the flexible portion of the shaft. In yet another alternative arrangement, the resilient member may have a flat surface such that the movement of the resilient member is substantially within a plane perpendicular to the flat surface. In yet another alternative arrangement, the first lumen of the guide bushing and the longitudinal axis of the hollow shaft may be parallel when the guide bushing is in the first position, and the first lumen of the guide bushing and longitudinal axis of the hollow tube may not be parallel when the guide bushing is in the second position. In yet another alternative arrangement, the device may include an elastomeric sleeve that covers the flexible portion of the shaft.

In accordance with another embodiment, a device for delivering a medical aid into a patient may include a hollow shaft having a proximal end, a distal end having an inner surface at the distal end, a longitudinal axis, and a flexible portion between the proximal and distal ends in which the flexible portion may be capable of bending away from the longitudinal axis. The device may further include a pull wire having a proximal end and a distal end mechanically coupled to the inner surface and a flexible tube capable of passing through the inner surface at the distal end of the hollow shaft in which the flexible tube may have a second lumen. The distal end of the hollow shaft may be in a first position when the distal end of the pull wire is in a first position and the distal end of the hollow shaft may be in a second position when the distal end of the pull wire is in a second position.

In an alternative arrangement, the flexible tube may be in a first position when the distal end of the pull wire is in a first position, and the flexible tube may be in a second position when the distal end of the pull wire is in a second position. In another alternative arrangement, the hollow shaft may have an interior surface along a portion of its length and proximal to the inner surface of the hollow shaft. In such an arrangement, the device may include a resilient member attached to the interior surface of the hollow shaft on proximal and distal sides of the flexible portion of the shaft. In yet another alternative arrangement, the resilient member may have a flat surface such that movement of the resilient member is substantially within a plane perpendicular to the flat surface. In yet another alternative arrangement, an axis through the distal end of the hollow shaft and an axis through the proximal end of the hollow shaft may be parallel when the distal end of the hollow shaft is in the first position and the axes of the distal end of the hollow shaft and the proximal end of the hollow tube are not parallel when the distal end of the hollow tube is in the second position. In yet another alternative arrangement, the device may further include an elastomeric sleeve that covers the flexible portion.

BRIEF DESCRIPTION OF THE DRAWINGS

Various embodiments of the present invention will now be discussed with reference to the appended drawings. It will be appreciated that these drawings depict only some embodiments of the invention and are therefore not to be considered limiting of its scope.

FIG. 3 is a cross-sectional view of a portion of the delivery device of FIG. 2A, shown in a first position;

FIG. 4A is a cross-sectional view of the portion of the delivery device of FIG. 2A, shown in a second position;

FIG. 6A is a plan view of a delivery device in accordance with another embodiment of the invention, shown in a first position;

FIG. 6B is a plan view of the delivery device of FIG. 6A, shown in a second position;

FIG. 7 is an exploded view of a portion of the delivery device of FIG. 6A;

DETAILED DESCRIPTION

In the present application, reference is made to particular features of the invention. It is to be understood that the disclosure of the invention in this application is intended to include all possible combinations of such features, whether or not such combinations have been particularly described. For example, where a feature is disclosed in the context of a particular aspect, arrangement, or embodiment of the invention, that feature can also be used, to the extent possible, in combination with and/or in the context of other aspects, arrangements, and embodiments of the invention described herein.

The term "at least" followed by a number is used herein to denote the start of a range beginning with that number (which can be a range having an upper limit or no upper limit, depending on the variable being defined). For example, "at least 1" means 1 or more than 1.

As used herein, the terms "proximal" and "distal" are to be taken as relative to a user (e.g., a surgeon or an interventional cardiologist) of the delivery devices disclosed herein. "Proximal" is to be understood as relatively close to the user and "distal" is to be understood as relatively farther away from the user.

Figure 1:
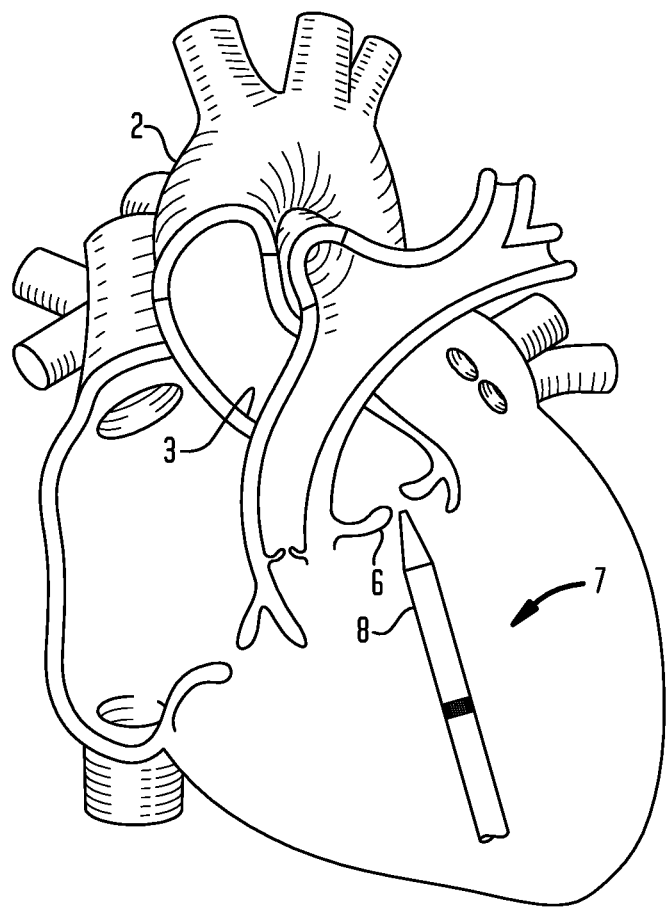
FIG. 1 is a diagrammatic view showing the use of a conventional transapical delivery device to deliver a collapsible prosthetic heart valve to the aortic valve annulus.
Figure 2A:
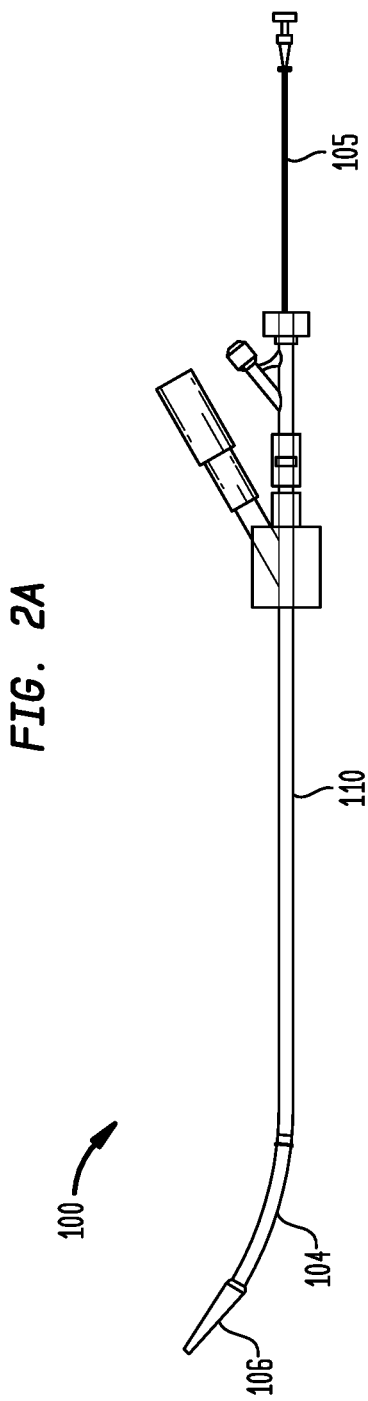
FIG. 2A is a plan view of a delivery device in accordance with one embodiment of the invention.
Figure 2B:
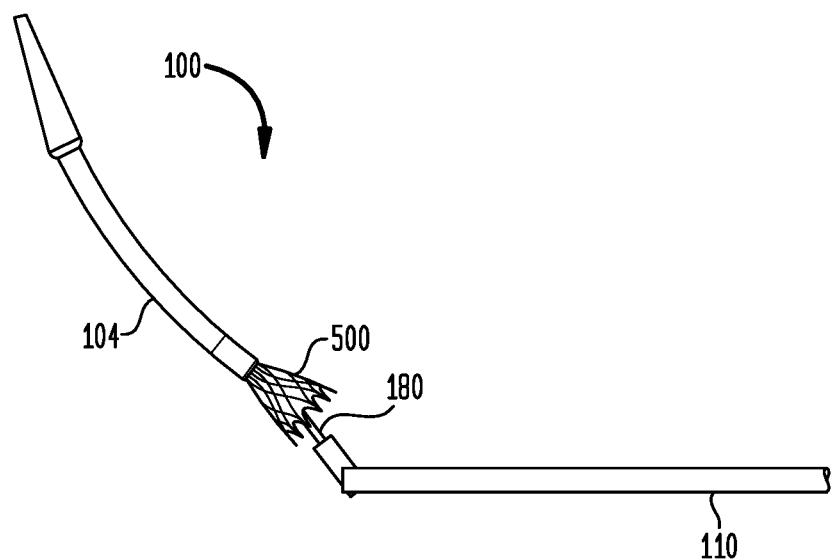
FIG. 2B is a plan view of a distal portion of the delivery device of FIG. 2A showing a prosthetic heart valve being deployed.

Referring now to the example shown in FIGS. 2A and 2B, in one embodiment, a delivery device 100 may include on a generally proximal end of the device 100 an elongated shaft 110 having a lumen along a longitudinal axis of the shaft 110 and on a generally distal end of the device 100 an elongated sheath 104 having a lumen along a longitudinal axis of the sheath 104. The sheath 104 may be straight or, as in the example shown in FIGS. 2A and 2B, may be curved to conform to the contour of an aorta during insertion of the device 100 through the aortic annulus as part of a transapical valve implantation procedure. Such a curvature is believed to reduce the risk of damage to the inner wall of the aorta.

Figure 4B:
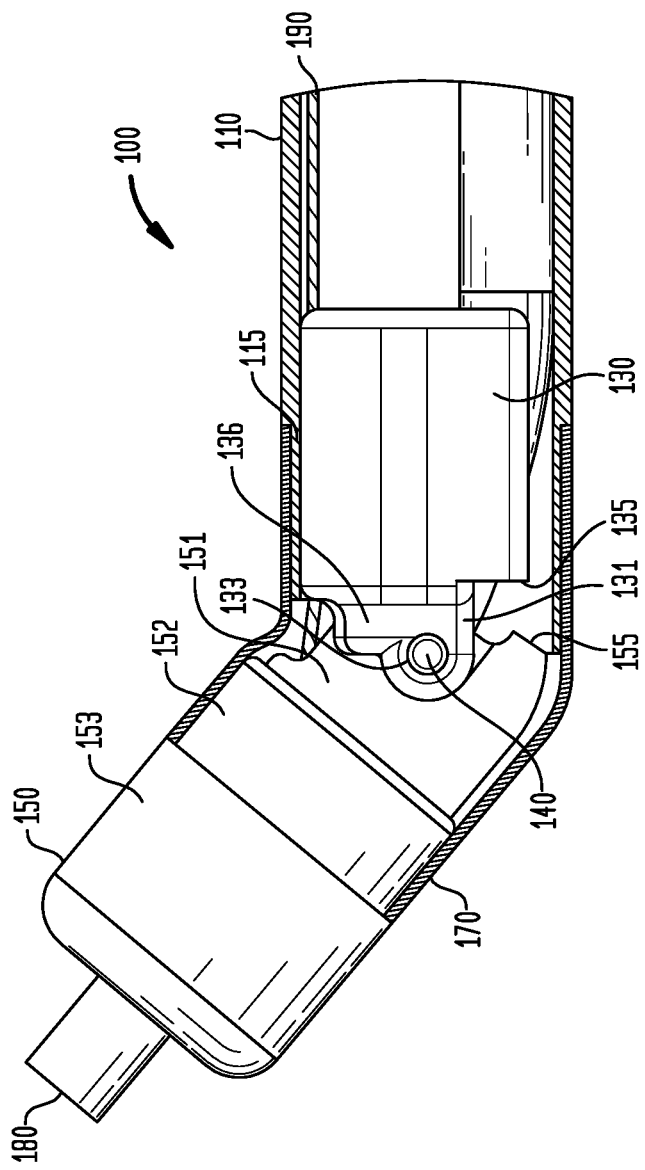
FIG. 4B is a side view, partially broken away, of the portion of the delivery device shown in FIG. 4A, shown in the second position.

Referring to FIGS. 3, 4A, and 4B, the shaft 110 may be a rigid shaft. To provide this rigidity, in some embodiments, the shaft 110 may be made of a biologically compatible steel which may be, but is not limited to 304 stainless steel, or other rigid materials. The shaft may have a mating segment 115 on a distal end having a smaller diameter than the rest of the shaft, as discussed further herein. Located within the lumen at the distal end of the shaft 110 may be a pivot anchor 130 having upper and lower portions 132, 134 along a longitudinal axis of the anchor 130. The pivot anchor 130 may be welded to the shaft 110 in order to fix the position of the anchor 130 relative to the shaft 110. As best shown in FIG. 4B, on the distal end of the pivot anchor 130 may be an engagement portion 131. As shown in FIGS. 3, 4, and 4B, the engagement portion 131 may include a first flange 136 having a hole 133 through its thickness opposite a second flange (not shown) also having a hole (not shown) through its thickness in a direction transverse to the longitudinal axis of the pivot anchor 130.

As further shown in FIGS. 3, 4, and 4B, a pivot arm 150 may have a lumen along its longitudinal axis, a first arm portion 151 on its proximal end having a diameter, a second arm portion 152 adjacent to the first arm portion 151 having a diameter greater than the first arm portion 151, and a third arm portion 153 adjacent the second arm portion 152 on its distal end having a diameter greater than the second arm portion 152. The first arm portion 151 may further have opposing blind holes through its thickness in a transverse direction to the longitudinal axis of the pivot arm 150. As best shown in FIG. 4B, the diameter of the first arm portion 151 may be sized to fit between the first flange 136 and the opposing second flange of the engagement portion 131 of the pivot anchor 130. Still referring to FIG. 4B, each of the holes through the pivot anchor 130 may be aligned with the respective blind holes of the first arm portion 151 of the pivot arm 150. Pins 140 may be inserted through the aligned holes to allow the pivot arm 150 to rotate within only a single plane relative to the pivot anchor 130. The pivot anchor 130 may further have an anchor stop 135 and the pivot arm 150 may have a corresponding arm stop 155 that do not contact each other when the pivot arm 150 is rotated about the pins 140, such as in the example of FIGS. 4A and 4B, but that do contact each other when the pivot arm 150 is in a straight position, such as in the example of FIG. 3, to function as a positive stop. By placing the anchor stop 135 and the arm stop 155 on only one side of the respective pivot anchor 130 and pivot arm 150, rotation of the pivot arm 150 may be limited to only one direction. In alternative arrangements, the positive stop may be eliminated to allow rotation of the pivot arm 150 in opposite directions.

As shown in FIGS. 3, 4A, and 4B, the distal end of a sleeve 170 may be placed around the second arm portion 152 and may abut the third arm portion 153 of the pivot arm 150. The proximal end of the sleeve 170 may be placed around the mating segment 115. In some arrangements, the sleeve 170 may be sized to engage either or both of the second arm portion 152 and the mating segment 115 in a tight interference fit. In other arrangements, the sleeve 170 may be bonded to the second arm portion 152 and the mating segment 115, e.g., by epoxy or other adhesive, ultrasonic welding and the like. The sleeve 170 may be flexible to allow it to bend during rotation of the pivot arm 150 relative to the pivot anchor 130. As such, the sleeve 170 may be made of an elastomeric material such as a polymer.

As best shown in FIGS. 3 and 4A, a tube 180 may extend from a position beyond the distal end of the pivot arm 150, through the lumen of the pivot arm 150, and through the pivot anchor 130. As demonstrated in FIG. 4A, the tube 180 may be flexible. In some arrangements, the tube 180 may be a metal coil, e.g., a multi-stranded, helically wound or braided coil, and in some other arrangements may be a plastic tube having a flexible portion along at least a segment of the tube. The tube 180 may have an outer diameter that is substantially equal to the diameter of the lumen of the pivot arm 150 such that, upon rotation of the pivot arm 150, the tube 180 bends near the interface of the pivot anchor 130 and the pivot arm 150. The distal end of the tube 180 may be inserted into a retainer (not shown) used to retain a prosthetic heart valve. The tube 180 may be fixed to the retainer through any process well-known to those of ordinary skill in the art, such as an interference fit, an adhesive bond, or a combination of such processes. When a retainer is situated within a distal sheath, such as the sheath 104 shown in FIGS. 2A and 2B, in a manner known to those of ordinary skill in the art, rotation of the tube 180 causes a corresponding rotation of the distal sheath.

As best shown in FIGS. 3 and 4A, a pull wire 190 may be attached at its distal end to the pivot arm 150. In some arrangements, the pivot arm 150 may be made of a metal, such as stainless steel, to which the pull wire 190 may be welded. In some other arrangements, the pull wire 190 may be inserted into a counterbore within the pivot arm 150 and crimped or held in place by a set screw inserted into the pivot arm 150. The pull wire 190 may extend to substantially the proximal end of the shaft 110 where it may be actuated directly or indirectly by the user. The pull wire 110 may be attached to the pivot arm 150 at a position a distance away from the central axis of the pivot arm 150 such that, upon actuation by a user, the pull wire 190 may be pulled in the proximal direction to cause the pivot arm 150, and thus the tube 180 inserted in the arm 150, to rotate about pins 140 relative to the pivot anchor 130 due to the torque exerted by the pulling action. Accordingly, in the example shown in FIGS. 3, 4A, and 4B, pulling the wire 190 causes the sheath 104 that is mechanically coupled to the tube 180 to rotate. In this manner, during a transapical prosthetic valve procedure, the device 100 may be inserted through the apex of the heart in a straight configuration, such as in the example of FIG. 3. After the sheath 104 passes through the apex, the user may actuate the pull wire 190 to cause the sheath 104 to rotate about the pivot pins 140, as in the example of FIGS. 4A and 4B, to various angular orientations including an orientation that is substantially perpendicular to the aortic annulus.

Referring again to FIGS. 2A and 2B, a deployment wire 105 may be inserted through the shaft 110, the tube 180, and the sheath 104. The deployment wire 105 may further be inserted into a cavity (not shown) of a tip 106 on the distal end of the sheath 104 as known to those of ordinary skill in the art. In this manner, once the sheath 104 is fully inserted through the aortic annulus, the deployment wire 105 may be pushed in a distal direction against the cavity of the tip 106 such that the sheath 104 is moved in the distal direction and separated from the shaft 110. During this movement, the tube 180 remains substantially stationary. As shown in FIG. 2B, a valve 500, such as a collapsible prosthetic heart valve (or other type of self-expanding collapsible stents) known to those of ordinary skill in the art, may surround at least a portion of the tube 180. In the example of FIG. 2B, the valve 500 is fixed to a retainer that is itself fixed to the distal end of the tube 180. As further shown by comparing FIGS. 2A and 2B, the valve 500 expands as it becomes uncovered by the distal movement of the sheath 104. After deployment of the valve 500 and its engagement in the aortic annulus, the deployment wire 105 may be pulled in the proximal direction to retract the sheath 104 which can then be passed through the now deployed valve 500.

Figure 5:
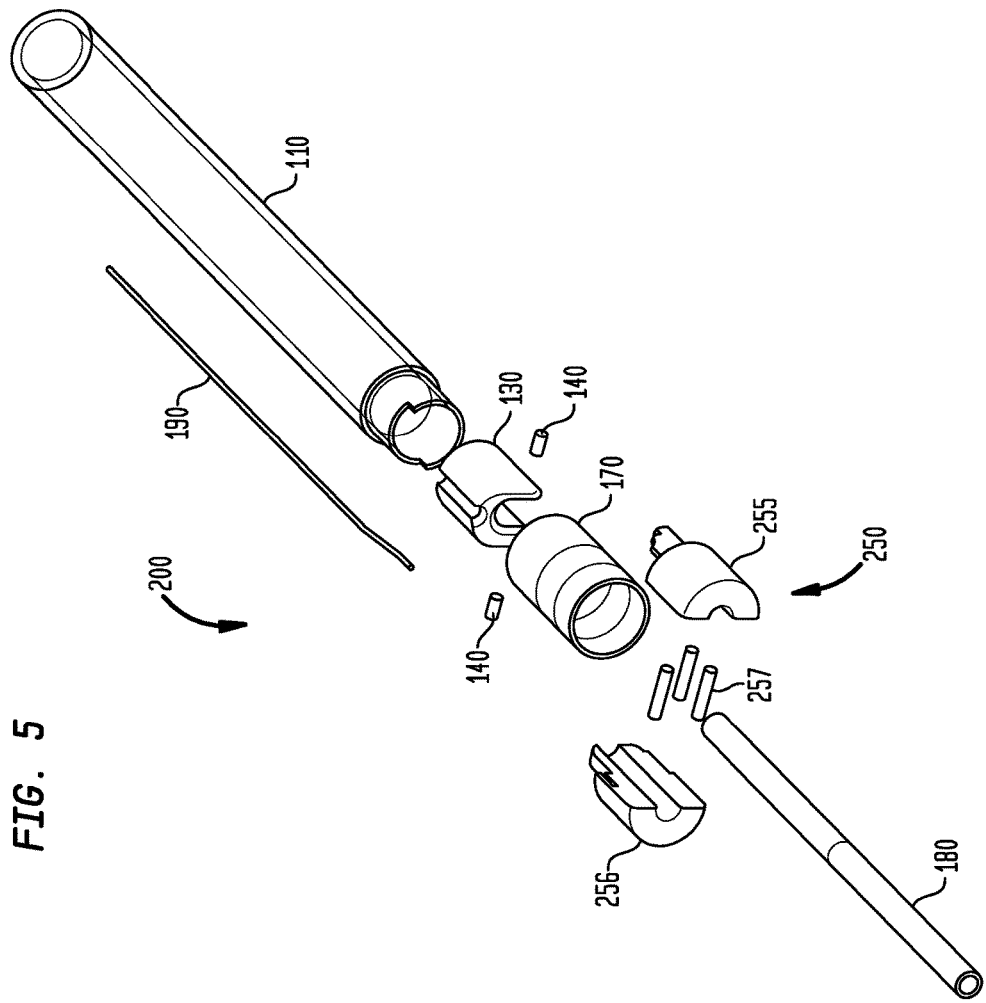
FIG. 5 is an exploded view of a portion of a delivery device in accordance with another embodiment of the invention.

Referring now to FIG. 5, in an alternative arrangement, a delivery device 200 may include identical features to the features of the delivery device 100 just described, except that the device 200 may incorporate a pivot arm 250. As shown in the example of FIG. 5, the pivot arm 250 may be a two-piece assembly having a first segment 255 and a second segment 256 that may be held together by pins 257 inserted into apertures in each of the segments 255, 256. When assembled, the pivot arm 250 may be substantially similar to pivot arm 150, and thus may have a lumen and first, second, and third arm portions similar to those described above.

In another embodiment, such as in the example shown in FIGS. 6A and 6B, a delivery device 300 may include on a generally proximal end an elongated shaft 310 having a lumen along a longitudinal axis of the shaft 310 and on a generally distal end of the device 300 an elongated sheath 304 having a lumen along a longitudinal axis of the sheath 304. The sheath 304 may be substantially similar to the sheath 104 previously described herein. Additionally, the sheath 304 may be attached to a tube, such as a tube 380 described further herein, in a manner substantially similar to the attachment of the sheath 104 to the tube 180. The tube 2380 may be substantially similar to the tube 180 previously described herein.

Figure 8:
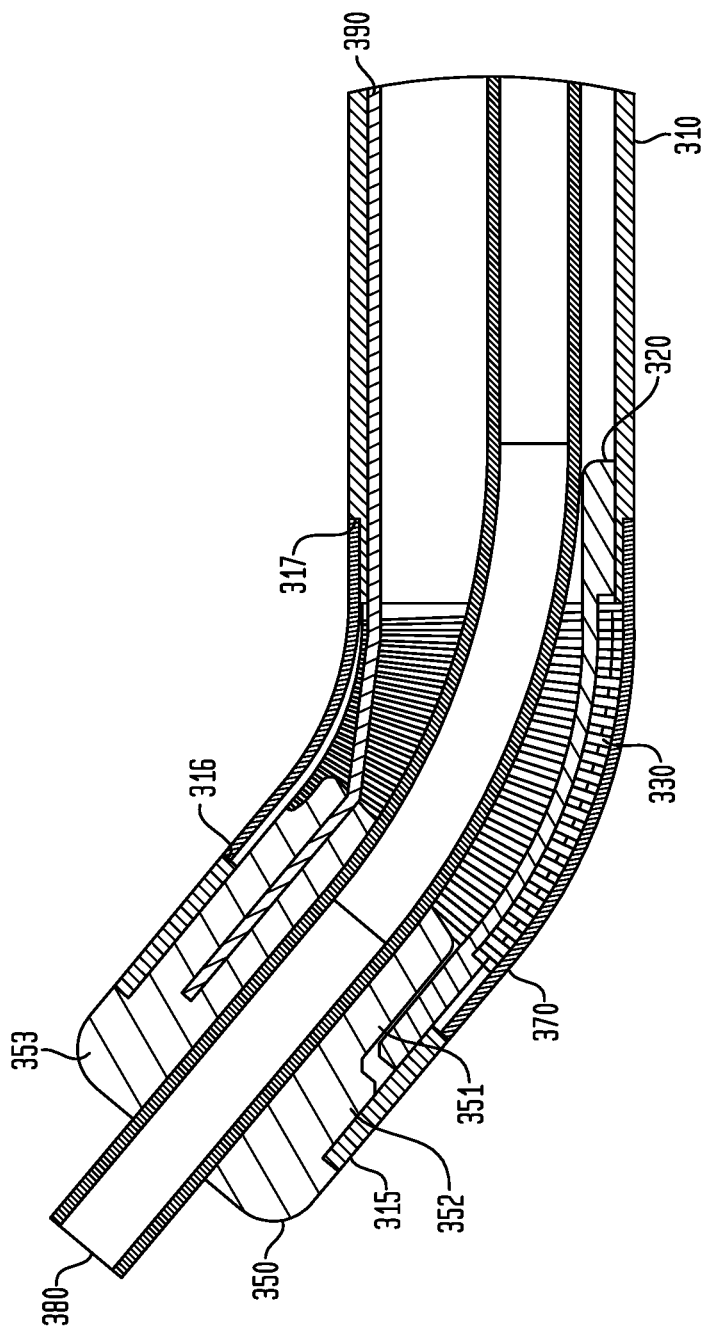
FIG. 8 is a cross-sectional view of a portion of the delivery device of FIG. 6A.

As illustrated in FIGS. 7 and 8, the shaft 310 may have a flexible portion 330 adjacent a distal end of the shaft 310. The shaft 310 may be made of a biologically compatible steel. In this instance, the flexible portion 330 may be formed by making continuous spiral cuts along a portion of the shaft 310 to create a coil. These cuts may be made by laser machining the portion intended to be flexible. However, other methods of forming the flexible portion may be utilized. As further shown in FIGS. 7 and 8, the diameter of the flexible portion 330 may be less than the diameter of the remainder of the shaft. In this instance, the flexible portion 330 may be located between a face 316, formed at the interface of the distal end of the flexible portion 330 and a mating portion 315 on the distal end of the shaft 310, and a face 317, formed at the interface of the proximal end of the portion 330 and the more proximal end of the shaft 310.

As shown in FIG. 8, a sleeve 370 may be placed around the flexible portion 330. In this example, the sleeve 370 may extend from the face 316 to the face 317 and may have a thickness such that upon placement of the sleeve 370 around the flexible portion 330, the diameter of the sleeve 370 is substantially equal to the diameter of the remainder of the shaft 310. In this manner, the sleeve 370 may fit tightly around the flexible portion 330 to prevent blood leakage through the flexible portion 330. The sleeve 370 may be flexible in the same manner as the sleeve 170 described previously herein.

As the flexible portion 330 allows the shaft 310 to articulate on the distal end of the shaft 310, a resilient member 320 may be attached on its distal end to the mating portion 315 of the shaft 310 and on its proximal end to the proximal portion of the shaft 310, as best shown in FIG. 8. The resilient member 320 may be attached to the shaft 310 by welding or by other known processes for fixing components together. As further shown in the example of FIGS. 7 and 8, the resilient member 320 may be a flat spring that restricts bending movement in a first plane parallel to the largest opposing surfaces of the flat spring more than it restricts movement in the plane perpendicular to the first plane. In this manner, articulation of the shaft 310 may be substantially limited to movement in the direction perpendicular to the first plane.

As best shown in FIG. 8, a bushing 350 may have a bore along its longitudinal axis. The bushing 350 may further have a first bushing portion 351 on a proximal end having a diameter in a direction transverse to the longitudinal axis, a second bushing portion 352 adjacent to and having a diameter greater than the diameter of the first bushing portion 351, and a third bushing portion 353 on a distal end and adjacent to and having a width greater than the width of the second bushing portion 352. The third bushing portion 353 may abut mating portion 315 on the distal end of the shaft 310 such that the bushing 350 is partially inserted into the shaft 310 and has its bore in fixed alignment with the longitudinal axis of the shaft 310. The first bushing portion 351 may be formed with a recess such that there is a space between the first bushing portion 351 and the shaft 310. In this manner, the distal end of the resilient member 320 may be attached to the shaft 310 at a position overlapping the bushing 350 along the longitudinal axis of the shaft 310 without contacting the bushing 350.

As further shown in FIG. 8, a pull wire 390 may be attached on its distal end to the bushing 350 in the same manner as the pull wire 190 may be attached to the pivot arm 150 as described previously herein. The pull wire 390 may extend to the proximal end of the device 300 where it may be actuated by the user in the same manner as that described previously herein for the pull wire 190. A tube 380 may be inserted through the bore of the bushing 350 and extend completely through the flexible portion 330. As the tube 380 may have substantially the same features as those described previously herein for tube 180, the tube 380 may be flexed during articulation of the flexible portion 330. Accordingly, upon actuation by the user, the pull wire 390 may be pulled in the proximal direction causing the bushing 350, and hence the distal end of the tube 380 that is inserted within the bushing 350, to rotate about the flexible portion 330 within a single plane due to the resistance of the resilient member 320. The distal end of the tube 380 may be mechanically coupled to the sheath 304 such that rotation of the bushing 350 results in a corresponding angular displacement of the sheath 304, as shown in FIG. 6B. Thus, pulling the wire 390 causes the sheath 304 to rotate.

Figure 9:
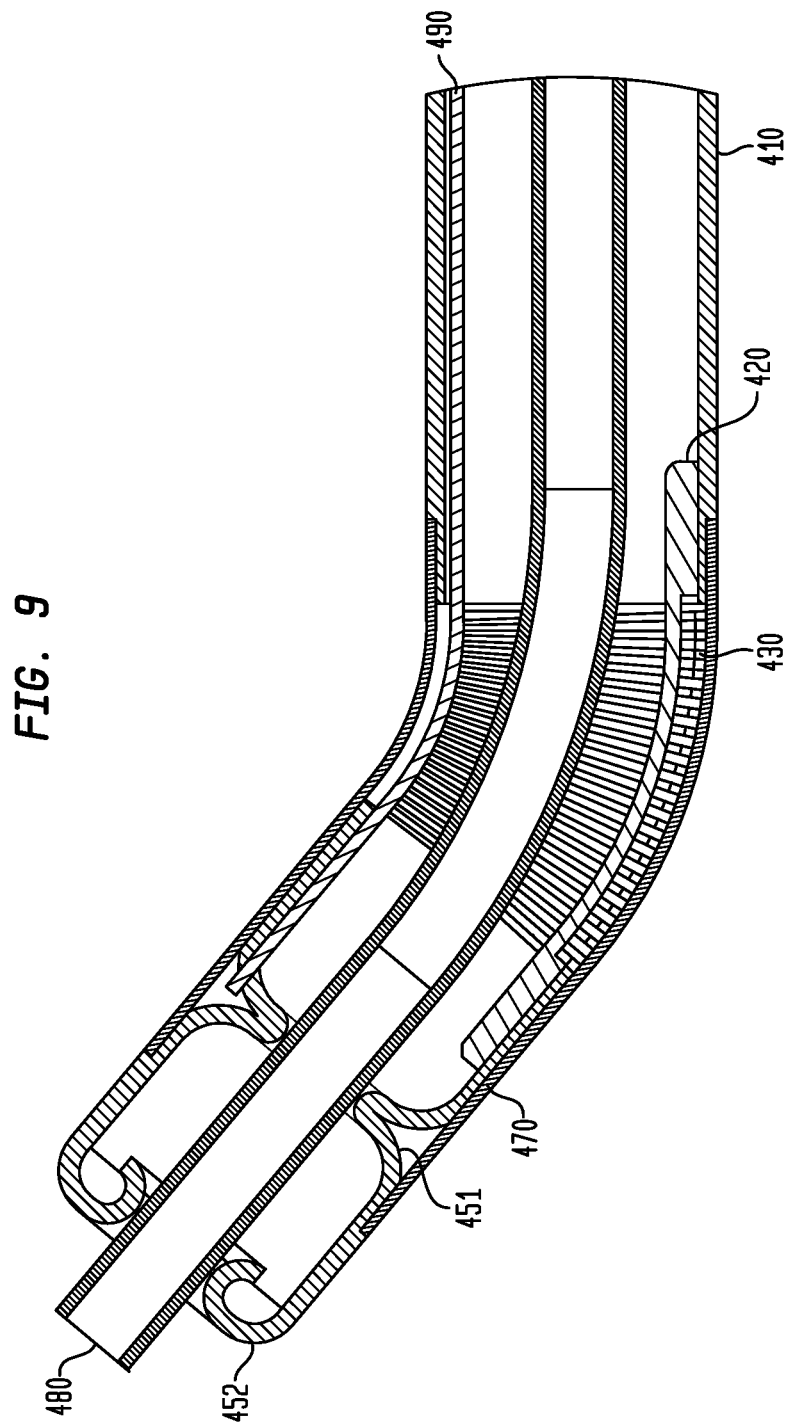
FIG. 9 is a cross-sectional view of a delivery device in accordance with another embodiment of the invention.

In an alternative arrangement shown in FIG. 9, a delivery device 400 may have substantially the same features as the device 300 with some notable exceptions. The device 400 may have a resilient member 420, a flexible portion 430, a sleeve 470, a tube 480, and a pull wire 490 that are substantially the same as the resilient member 320, the flexible portion 330, the sleeve 370, the tube 380, and the pull wire 390, respectively, used in the device 300. Moreover, the device 400 may have a shaft 410 that is similar in size and shape to and provides the same functions as the shaft 310 from the proximal end of the shaft 410 to the location of the attachment of the resilient member 320 to the shaft 410. However, in this arrangement, the shaft 410 may be bent to form at least one inner diameter portion of the shaft 410 such that the inner diameter portion of the shaft 410 contacts or nearly contacts a corresponding portion of the tube 480. In this manner, the shaft 410 may act as a guide bushing for the tube 480. For example, as shown in FIG. 8, the shaft 410 may have a first crimp 451 and a second crimp 452 distal to the flexible portion 430 that may maintain the portion of the tube 480 distal to the first crimp 451 in a longitudinally straight position during articulation of the shaft 410 about the flexible portion 430.

As shown in FIG. 9, the pull wire 490 may be attached on its distal end to the distal end of the shaft 410. The pull wire 490 may be attached the first crimp 451 at a location a distance away from a central longitudinal axis of the shaft 410. The pull wire 490 may extend to the proximal end of the device 400 where it may be actuated by the user in the same manner as that described previously herein for the pull wire 190. Accordingly, upon actuation by a user, the pull wire 490 may be pulled in the proximal direction causing the first crimp 451, and hence the tube 480 and sheath (not shown) attached to the tube 480 by a spacer rod (not shown), to rotate about the flexible portion 430 within a single plane due to the resistance of the resilient member 420.

The articulation features just described may be used by a user of the devices 300 and 400 to align the respective sheaths of these devices with the aortic annulus in the same manner as that described previously herein for the device 100.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A device for delivering a medical aid into a patient, the device comprising:
   a hollow shaft having proximal and distal ends, a longitudinal axis, and flexible and rigid portions between the proximal and distal ends, the flexible portion being configured to bend away from the longitudinal axis and the hollow shaft distal end having an end face;
   a guide bushing having a first lumen, an exterior surface, and a body defined between the first lumen and the exterior surface, a portion of the exterior surface of the guide bushing abutting the end face of the hollow shaft distal end;
   a pull wire directly attached to and extending within the body of the guide bushing;
   a flexible tube extending through the first lumen of the guide bushing; and
   a sheath mechanically coupled to the flexible tube, the sheath surrounding a distal end of the flexible tube in a first position and being slidable to a second position to expose the distal end of the flexible tube,
   wherein the guide bushing is in a first position when the pull wire is in a first position and the guide bushing is in a second position when the pull wire is in a second position.

2. The device of claim 1, further comprising a resilient member extending through the flexible portion of the hollow shaft and attached to proximal and distal portions of the hollow shaft.

3. The device of claim 2, wherein the resilient member is a spring having a flat surface such that movement of the resilient member is substantially within a plane perpendicular to the flat surface.

4. A device for delivering a medical aid into a patient, the device comprising:
   a hollow shaft having a proximal portion including a proximal end, a distal portion including a distal end, and flexible and rigid portions between the proximal and distal ends, the hollow shaft proximal portion having a longitudinal axis and the flexible portion being configured to bend away from the longitudinal axis;
   a pull wire mechanically coupled to the hollow shaft;
   a flexible tube extending through the distal portion of the hollow shaft a guide bushing having a first lumen, an exterior surface, and a body defined between the first lumen and the exterior surface, the exterior surface of the guide bushing being sized to matingly engage an interior surface of the hollow shaft distal portion; and
   a sheath mechanically coupled to the flexible tube, the sheath surrounding a distal end of the flexible tube in a first position, and the sheath being slidable to a second position exposing the distal end of the flexible tube,
   wherein the hollow shaft distal portion is in a first position when the pull wire is in a first position and the hollow shaft distal portion is in a second position when the pull wire is in a second position, and wherein the pull wire extends within the body of the guide bushing.

5. The device of claim 4, wherein the flexible tube is in a first position when the pull wire is in the first position and the flexible tube is in a second position when the pull wire is in the second position.

6. The device of claim 4, wherein the hollow shaft distal portion has a central axis, the central axis and the longitudinal axis of the hollow shaft proximal portion being parallel when the hollow shaft distal portion is in the first position, and the central axis and the longitudinal axis of the hollow shaft proximal portion being transverse to each other when the hollow shaft distal portion is in the second position.

7. The device of claim 4, further comprising an elastomeric sleeve that tightly covers the flexible portion of the hollow shaft to prevent blood leakage through the flexible portion.

8. The device of claim 4, further comprising a valve assembled on the flexible tube, wherein the valve is in a first position when the pull wire is in the first position and the valve is in a second position when the pull wire is in the second position.

9. The device of claim 8, further comprising a sheath slidable relative to the flexible tube between a first position in which the sheath surrounds the valve and holds the valve in a contained configuration and a second position in which the sheath exposes the valve for deployment.

10. The device of claim 4, wherein the distal portion has an inner surface along a part of a length thereof defining an inner lumen having a smaller perimeter than a rest of the length of the inner surface of the hollow shaft.

11. The device of claim 4, further comprising:
    a spring attached to the proximal and distal portions of the hollow shaft and extending through the flexible portion of the hollow shaft, wherein the spring has a surface that defines a plane parallel to the longitudinal axis when the hollow shaft distal portion is in the first position such that movement of the spring is substantially within a plane perpendicular to the surface.

12. A device for delivering a medical aid into a patient, the device comprising: a hollow shaft having a proximal portion including a proximal end, a distal portion including a distal end, and flexible and rigid portions between the proximal and distal ends, the hollow shaft proximal portion having a longitudinal axis and the flexible portion being configured to bend away from the longitudinal axis; a pull wire mechanically coupled to the hollow shaft; a flexible tube extending through the distal portion of the hollow shaft; and a sheath mechanically coupled to the flexible tube, the sheath surrounding a distal end of the flexible tube in a first position, and the sheath being slidable to a second position exposing the distal end of the flexible tube, wherein the hollow shaft distal portion is in a first position when the pull wire is in a first position and the hollow shaft distal portion is in a second position when the pull wire is in a second position, and wherein the flexible portion is in a form of a coil.

13. The device of claim 12, wherein the coiled flexible portion is formed by a continuous spiral cut along the hollow shaft.

14. The device of claim 12, further comprising a guide bushing having a first lumen, an exterior surface, and a body defined between the first lumen and the exterior surface, the exterior surface of the guide bushing being sized to matingly engage an interior surface of the distal portion of the hollow shaft.

15. The device of claim 14, wherein the pull wire extends within the body of the guide bushing.

16. A device for delivering a medical aid into a patient, the device comprising:
  a hollow shaft having proximal and distal ends, a longitudinal axis, and flexible and rigid portions between the proximal and distal ends, the flexible portion being configured to bend away from the longitudinal axis;
  a guide bushing having a first lumen, the guide bushing being sized to matingly engage the hollow shaft distal end;
  a pull wire directly and fixedly attached to the guide bushing;
  a flexible tube extending through the first lumen of the guide bushing; and
  a sheath mechanically coupled to the flexible tube, the sheath surrounding a distal end of the flexible tube in a first position and the sheath being slidable to a second position exposing the distal end of the flexible tube,
  wherein the guide bushing is in a first position when the pull wire is in a first position and the guide bushing is in a second position when the pull wire is in a second position.

17. The device of claim 16, wherein the flexible tube is in a first position when the pull wire is in the first position and the flexible tube is in a second position when the pull wire is in the second position.

18. The device of claim 16, wherein the first lumen of the guide bushing has a central axis, the central axis of the first lumen and the longitudinal axis of the hollow shaft being parallel when the guide bushing is in the first position, and the central axis of the first lumen and the longitudinal axis of the hollow shaft being transverse to each other when the guide bushing is in the second position.

19. The device of claim 16, further comprising an elastomeric sleeve that tightly covers the flexible portion of the hollow shaft to prevent blood leakage through the flexible portion.

20. The device of claim 16, further comprising a valve assembled on the flexible tube, wherein the valve is in a first position when the pull wire is in the first position and the valve is in a second position when the pull wire is in the second position.

21. The device of claim 20, wherein the sheath surrounds and holds the valve in a contained configuration when the sheath is in the first position and exposes the valve for deployment when the sheath is in the second position.

22. The device of claim 16, wherein the flexible portion is in a form of a coil.

23. The device of claim 22, wherein the coiled flexible portion is formed by a continuous spiral cut along the hollow shaft.

24. The device of claim 16, further comprising a spring attached to the hollow shaft and extending through the flexible portion and having a surface that defines a plane parallel to the longitudinal axis when the pull wire is in a first position such that movement of the spring is substantially within a plane perpendicular to the surface.

25. The device of claim 16, wherein the second position of the sheath is distal to the first position.

* * * * *